United States Patent [19]

Marder et al.

[11] Patent Number: 5,500,156
[45] Date of Patent: Mar. 19, 1996

[54] UNSYMMETRICAL SQUARAINES FOR NONLINEAR OPTICAL MATERIALS

[75] Inventors: Seth R. Marder; Chin-Ti Chen, both of Pasadena, Calif.; Lap-Tak Cheng, Newark, Del.

[73] Assignee: California Institute of Technology, Pasadena, Calif.

[21] Appl. No.: 225,582

[22] Filed: Apr. 11, 1994

[51] Int. Cl.[6] .............................. F21V 9/00; C09K 19/00; H03F 7/00; C07C 49/293
[52] U.S. Cl. ...................... 252/582; 252/299.1; 359/328; 568/326; 568/327; 568/379; 568/381
[58] Field of Search .................................. 252/299.1, 582, 252/589; 568/306, 326, 329, 379, 381; 359/328

[56] References Cited

U.S. PATENT DOCUMENTS

| | | | |
|---|---|---|---|
| 4,886,722 | 12/1989 | Law et al. | 430/59 |
| 5,086,239 | 2/1992 | Wang | 359/328 |
| 5,106,713 | 4/1992 | Law | 430/59 |

OTHER PUBLICATIONS

112: 188649B Cyclobutenedione Derivative Nonlinear Optical Materials. Ueishi Kentaro; Fu, Ryujun (Fuji Xerox Co., Ltd.) Jpn. Kokai Tokkyo Koho JP 01,204,031 [89,204, 031], 16 Aug. 1989, Appl. 88/27,435, 10 Feb. 1988; 6 pp.

112: 181397j Unsymmetrical Squaraine Dyes. Law, Kock Yee; Bailey, F. Court (Xerox Corp.) Brit. UK Pat. Appl. GB 2,217,724, 01 Nov. 1989, US Appl. 187,777, 29 Apr. 1988; 25 pp.

Lee, Kock–Yee and Bailey, F. Court, Squaraine Chemistry. Synthesis, Characterization, and Optical Properties of a Class of Novel Unsymmetrical Squaraines: [4–(Dimethylamino)Phenyl](4'–Methoxyphenyl)Squaraine and Its Derivatives, J. Org. Chem. 1992, 57, 3278–3286.

*Primary Examiner*—Shean C. Wu
*Attorney, Agent, or Firm*—Poms, Smith, Lande & Rose

[57] ABSTRACT

Compositions for use in non-linear optical devices. The compositions have first molecular electronic hyperpolarizability ($\beta$) either positive or negative in sign and therefore display second order non-linear optical properties when incorporated into non-linear optical devices.

28 Claims, 1 Drawing Sheet

UNSYMMETRICAL SQUARAINES FOR NONLINEAR OPTICAL MATERIALS

The U.S. Government has certain rights in this invention pursuant to Contract No. CHE 9106689, National Science Foundation, and Contract No. AFOSR-ISSA-91-0070 awarded by the United States Air Force/Advanced Research Projects Agency. The invention described herein was made in the performance of work under a NASA contract, and is subject to the provisions of Public LAW 96-517 (35 USC 202) in which the Contractor has elected to retain title.

BACKGROUND OF THE INVENTION

1. Field of the Invention

The present invention relates generally to unsymmetrical squaraine dyes which exhibit nonlinear optical (NLO) properties. More particularly, the present invention relates to materials which have first molecular electronic hyperpolarizability ($\beta$) and therefore display second order nonlinear optical properties.

2. Description of Related Art

Organic materials that show second-order nonlinear optical responses are of interest for a variety of photonic and opto-electronic applications. See Marder, S. R., Sohn, J. E. & Stucky, G. D. eds. *Materials for Nonlinear Optics: Chemical Perspectives,* ACS Symposium Series, Vol. 455(American Chemical Society, Washington, 1991); Chemla, D. S. & Zyss, J. eds *Nonlinear optical properties of Organic Molecules and Crystals,* Vol. 1 and 2 (Academic Press, San Diego, 1987); and Williams, D. J. *Agnew. Chem. Int. Ed. Engl.* 23, 690–703 (1984).

Exemplary nonlinear optical materials and devices which utilize such materials are described in U.S. Pat. Nos. 5,062,693; 5,011,907; and 5,016,063. Nonlinear optical materials are also described in Japanese Patent Appln. No. 63-270834 filed Oct. 28, 1988, and published on May 2, 1990. Squaric acid derivatives which have been investigated for second harmonic generation include 1,2-disubstituted cyclobutene-3,4-diones. Exemplary materials have been described in Japanese Patent Appln. Nos. 89,204,031; 90,259,735; 91,71,117; 91,112,961; 92,199,135; 92,202,165; 92,202,166; and 92,202,167.

There is a continuing need to develop new materials which have sufficiently high second-order nonlinear optical properties when used in thin films and crystals to make them useful for applications such as telecommunications, optical data storage and optical information processing.

SUMMARY OF THE INVENTION

The present invention provides compositions of matter that have structures that are selected to provide first molecular electronic hyperpolarizability ($\beta$). It was discovered in accordance with the present invention that certain unsymmetrical squaraines, 2,4-disubstituted 3-oxo-1-cyclobutenolates, that can be viewed as unsymmetric cyanines, have unexpectedly large $\beta$. Compositions in accordance with the present invention have the general formula:

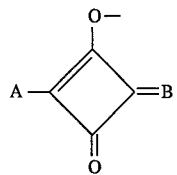

wherein A and B are different substituted compounds which give the squaraine unexpectedly large $\beta$.

A first group (Group I) of compounds in accordance with the present invention includes squaraines where

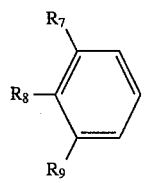

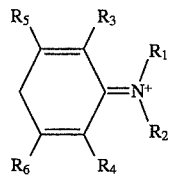

The general formula for Group I compounds is as follows:

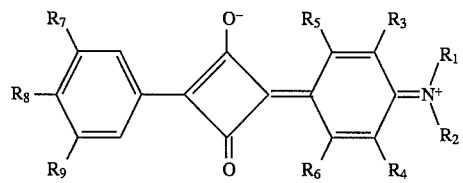

wherein $R_1$ is alkyl,$(CH_2)_n OH$ where n=1–8, $(CH_2)_n SH$ where n=1–8, phenylmethyl, 4-halophenylmethyl or $R_1+R_3=(CH_2)_3$; $R_2$ is alkyl, $(CH_2)_n OH$ where n=1–8, $(CH_2)_n SH$ where n=1–8, phenylmethyl, 4-halophenylmethyl or $R_2+R_4=(CH_2)_3$; $R_1$ and $R_2$ is a cyclic amine of the form $N(CH_2)_n$ where n=3–10; $R_3$ is H or $R_3+R_1=(CH_2)_3$; $R_4$ is H or $R_4+R_2=(CH_2)_3$; $R_5$ is H, F, OH, SH, $CH_3$, $C_2H_5$, $OCH_3$, or $SCH_3$; $R_6$ is H, F, OH, SH, $CH_3$, $C_2H_5$, $OCH_3$, or $SCH_3$; $R_7$ is H, alkyloxy or aryloxy; $R_8$ is H, alkyloxy or aryloxy; and $R_9$ is H, alkyloxy or aryloxy.

A second group (Group II) of compounds in accordance with the present invention includes squaraines wherein

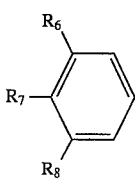

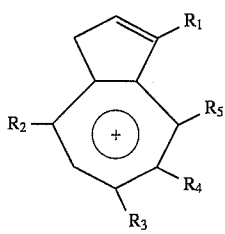

The formula for Group II compounds is as follows:

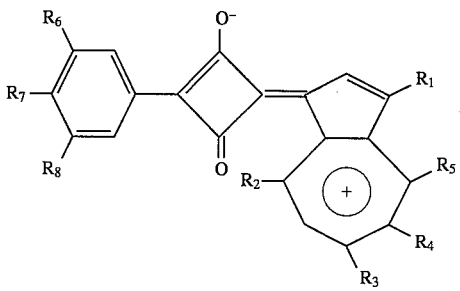

wherein $R_1$ is H or methyl; $R_2$ is H or methyl; $R_3$ is H or methyl; $R_4$ is H or isopropyl; $R_5$ is H or methyl; $R_6$ is H, alkyloxy or aryloxy; $R_7$ is H, $N(CH_3)_2$, alkyloxy or aryloxy; and $R_8$ is H, alkyloxy or aryloxy.

A third group (Group III) of compounds in accordance with the present invention includes squaraines wherein

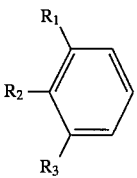

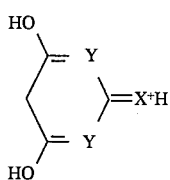

The general formula for Group III compounds is as follows:

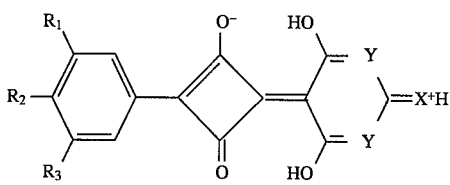

wherein X is O or S; Y is CH or N; $R_1$ is H, alkyloxy or aryloxy; $R_2$ is H, $N(CH_3)_2$, alkyloxy or aryloxy; and $R_3$ is H, alkyloxy or aryloxy.

A fourth group (Group IV) of compounds in accordance with the present invention includes squaraines wherein

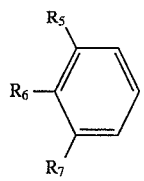

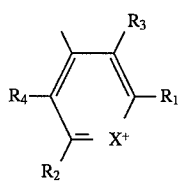

The formula for Group IV compounds is as follows:

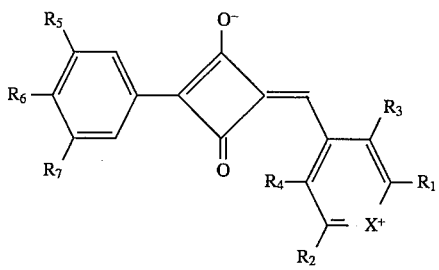

wherein X is NR where R=alkyl, $(CH_2)_n OH$ where n=1–8, or $(CH_2)_n SH$ where n=1–8, or where X is O, S, Se, or Te; $R_1$ and $R_2$ are H, tert-butyl, phenyl 4-toluyl; $R_3$ and $R_4$ are H or $R_1$ and $R_3$ is HC=CH—HC=CH and $R_2$ is phenyl, or $R_1$, $R_3$, $R_2$ and $R_4$ are HC=CH—HC=CH; $R_5$ is H, alkyloxy or aryloxy; $R_6$ is H, $N(CH_3)_2$, alkyloxy or aryloxy; and $R_7$ is H, alkyloxy or aryloxy.

A fifth group (Group V) of compounds in accordance with the present invention includes squaraines wherein

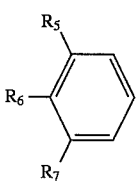

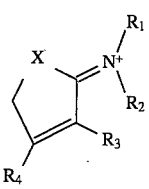

The formula for Group V compounds is as follows:

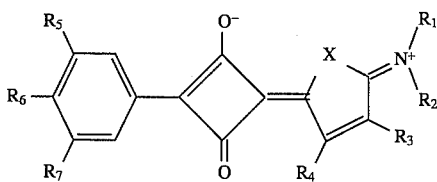

wherein $R_1$ and $R_2$ are $(CH_2)_2O(CH_2)_2$, $(CH_2)_4$, or $(CH_2)_5$; $R_3$ is H, phenyl, or 3-methoxyphenyl; $R_4$ is H, phenyl, 4-bromophenyl, or 2-chlorophenyl; $R_5$ is H, alkyloxy or aryloxy; $R_6$ is H, $N(CH_3)_2$, alkyloxy or aryloxy; $R_7$ is H, alkyloxy or aryloxy; and X is O, S, Se, or Te.

A sixth group (Group VI) of compounds in accordance with the present invention includes squaraines wherein

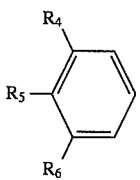

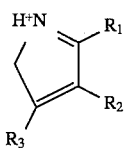

The formula for Group VI compounds is as follows:

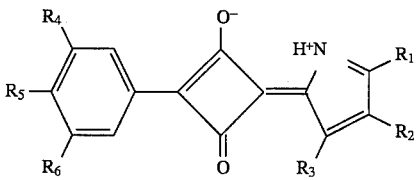

wherein $R_1$ is methyl, $R_2$ is H, alkyl, acetyl, or alkoxycarbonyl; $R_3$ is H or methyl; $R_4$ is H, alkyloxy or aryloxy; $R_5$ is H, $N(CH_3)_2$, alkyloxy or aryloxy; and $R_6$ is H, alkyloxy or aryloxy.

A seventh group (Group VII) of compounds in accordance with the present invention includes squaraines wherein

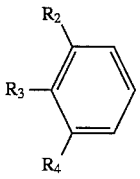

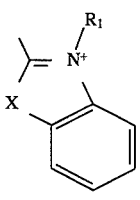

The formula for Group VII compounds is as follows:

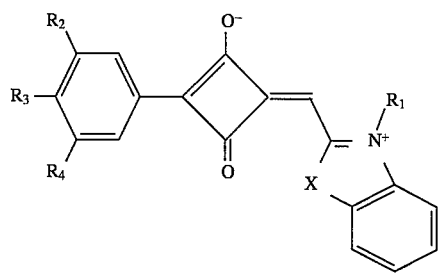

wherein $R_1$ is alkyl; X is HC=CH, $(CH_3)_2C$, O, S, or Se; $R_2$ is H, alkyloxy or aryloxy; $R_3$ is H, $N(CH_3)_2$, alkyloxy or aryloxy; and $R_4$ is H, alkyloxy or aryloxy.

An eighth group (Group VIII) of compounds in accordance with the present invention includes squaraines wherein

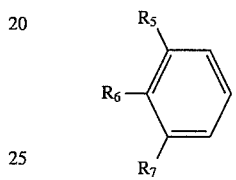

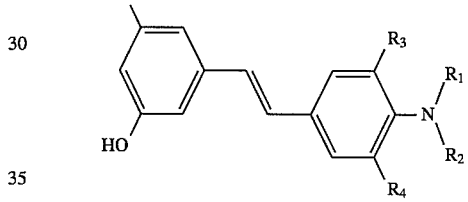

The formula for Group VIII compounds is as follows:

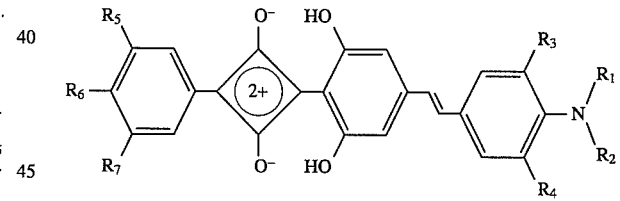

wherein $R_1$ is alkyl, $(CH_2)_nOH$ where n=1–8, $(CH_2)_nSH$ where n=1–8, phenylmethyl, 4-halophenylmethyl or $R_1+R_3=(CH_2)_3$; $R_2$ is alkyl, $(CH_2)_nOH$ where n=1–8, $(CH_2)_nSH$ where n=1–8, phenylmethyl, 4-halophenylmethyl or $R_2+R_4=(CH_2)_3$; $R_1$ and $R_2$ are a cyclic amine of the form $N((CH_2)_n$ where n=3–10; $R_3$ is H or $R_3+R_1=(CH_2)_3$; $R_4$ is H or $R_4+R_2=(CH_2)_3$; $R_5$ is H, alkyloxy or aryloxy; $R_6$ is H, $N(CH_3)_2$, alkyloxy or aryloxy; and $R_7$ is H, alkyloxy or aryloxy.

A ninth group (Group IX) of compounds in accordance with the present invention includes squaraines wherein

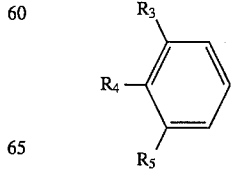

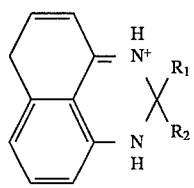

The formula for Group IX compounds is as follows:

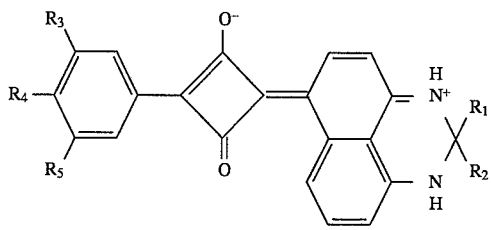

wherein $R_1$ is H, alkyl, $(CH_2)_nOH$ where n=1-8, $(CH_2)_nSH$ where n=1-8, phenylalkyl, phenyl, phenylcarbonyl, aryl, arylcarbonyl, arylalkyl, alkoxycarbonylalkyl, phenylcarbonylalkyl, or arylcarbonylalkyl.; $R_2$ is H, alkyl, $(CH_2)_nOH$ where n=1-8, $(CH_2)_nSH$ where n=1-8, phenylalkyl, phenyl, phenylcarbonyl, aryl, arylcarbonyl, arylalkyl, alkoxycarbonylalkyl, phenylcarbonylalkyl, or arylcarbonylalkyl.; $R_3$ is H, alkyloxy or aryloxy; $R_4$ is H, $N(CH_3)_2$, alkyloxy or aryloxy; and $R_5$ is H, alkyloxy or aryloxy.

As a feature of the present invention, nonlinear optical devices are provided which include compositions of matter which exhibit a high second-order nonlinear optical response.

Alkyl groups set forth in the above formulas include those groups having up to 10 carbon atoms and includes both branched and straight chain alkyl groups. Exemplary alkyl groups include methyl, ethyl, propyl, butyl, pentyl, hexyl, heptyl, octyl, nonyl, in the normal, secondary, iso and neo attachment isomers. Aryl groups referred to in the preceding formulas include aromatic hydrocarbons having up to 10 carbon atoms. Exemplary aryl groups include phenyl, naphthyl, furanyl, thiophenyl, pyrrolyl, selenophenyl, tellurophenyl.

Applicants' invention focuses on the importance of the conjugated π (pi)-electron bridge in determining second-order non-linear optical responses. The applicants have noted that molecules can be viewed as a linear combination of two limiting charge transfer resonance forms. If one form completely dominates, the molecules is designated as being polyene-like, if the two charge transfer resonance forms contribute equally the molecule is designated as being cyanine-like. It was discovered that there is an optimal linear combination of the two resonance form which is needed to maximize β. The β-value can be correlated to the bond-length difference, i.e., bond-length alternation (BLA), between the adjacent carbon-carbon bonds Thus as one goes from a polyen-like limit (BLA>–0.12 Å) to a cyanine-like limit (BLA=0 Å), β exhibits a peak at BLA—0.04 Å. Previous teachings typically focused on reaching this peak from the polyene limit which means having a BLA that is greater than –0.10 Å and therefore far from maximized β. In contrast, rather than starting near the polyene limit and decreasing the magnitude of BLA by searching for stronger donors or acceptors, to optimize β, we have considered introducing asymmetry into highly polarizable cyanine-like structures as an alternative strategy. In this manner, we seek to optimize β (in either a positive or negative peak) sense starting from the cyanine limit where BLA=0. Squaraine dyes are analogous to cyanine dyes in that they both have two degenerate resonance forms and both exhibit sharp and intense absorption band in visible or near IR region. However, unlike ionic cyanines, squaraines are neutral molecules that are suitable for electric-field-induced second harmonic generation (EFISH) measurement. In accordance with the present invention, we have developed synthetic strategies that lead to unsymmetric, soluble squaraines with significant β.

The above-discussed and many other features and attendant advantages will become better understood by reference to the following detailed description when taken in conjunction with the accompanying drawings.

DETAILED DESCRIPTION OF THE PREFERRED EMBODIMENT

Figure 1:
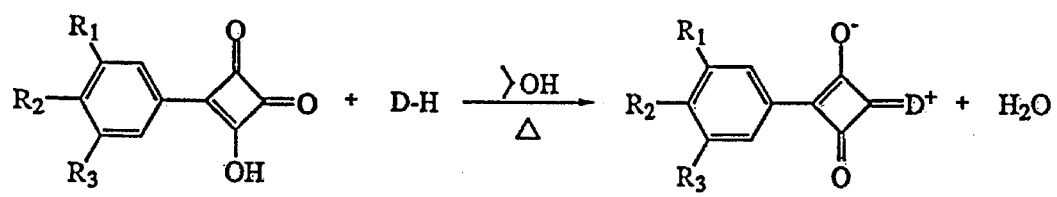
FIG. 1 is a schematic representation of the synthesis of an exemplary composition in accordance with the present invention wherein D-H is a neutral donor.

The compositions of the present invention are organic materials that show second-order non-linear optical responses. The compositions are incorporated into thin films and crystals in the same manner as other materials which exhibit non-linear optical properties. The compositions, themselves, may exist as crystals, liquids or gases. The compositions may be used alone or in combination with other materials which are conventionally used in nonlinear optical devices. Examples of devices in which the compositions of the present invention can be used include second-harmonic converters, spatial light modulators, parametric oscillators Mach-Zehnder Interferometers, and Fabry-Perot Interferometers.

The optical element in accordance with the invention may in some cases consist of a macroscopic crystal of the compound chosen, providing the compound can be made to form crystals in which the polar molecules are in noncentrosymmetric alignment. Such crystals may be grown at a slow rate under equilibrium with their mother liquor by a variety of methods practiced in the art. However, this procedure will not work for many polar molecules due in large part to dipole interactions. Another method of producing a useful optical element involves dissolving the compound in a solvent, which can be placed in a container having the desired shape. The solution can then be subjected to an electrical field which causes the dissolved dipoles to align themselves in the field. Electromagnetic radiation can then be passed through the solution and nonlinear optical effects, such as second harmonic generation, can be produced. Both the presence of an electric field and the need to utilize the compound in liquid solution form may be inconvenient or undesirable in some applications.

A particularly convenient and effective form of the optical element in accordance with the invention involves dispersing the polar molecules in a polymeric binder. The polar molecules can be mixed into the polymeric binder or grated onto the polymer. The mixture can be heated to a temperature at which the polymer becomes sufficiently soft so that upon application of an electrical field the polar molecules line up on the direction of the field. When the mixture cools, the polar molecules are locked into their aligned positions after which the electric field can be removed. Suitable binders include polymethacrylate, poly(methyl methacrylate), poly(vinyl alcohol), copolymers of methyl methacrylate and methacrylic acid, copolymers of styrene and maleic anhydride and half ester-acids of the latter, as well as many others. It is preferred that the polymeric binder of choice be highly transparent so that the transparency of the compounds utilized in the practice of this invention can be advantageously employed.

The poled polymer of this invention are considered particularly useful because of their high concentration of nonlinear optically active molecules, their capability of being formed into large area thin films, and their high orientational stability. Preferred film thickness can vary according to use. Typically film thickness is within the range of 0.5 μm–2 μm.

The poled polymer can also be provided in forms other than films (e.g., a solid block of polymer could be formed into an electrooptic modulator or a frequency converter using conventional techniques known in the art for single crystals) and poled polymer in various forms are included within this invention.

The poled polymers of this invention are preferably shaped to function as nonlinear optical elements for transforming electromagnetic radiation (e.g., by changing the frequency and/or polarization of the radiation). Generally, the nonlinear optical element of a poled polymer is used for transforming electromagnetic radiation by including it within an optical device. A device for transforming electromagnetic radiation using a nonlinear optical element is described in U.S. Pat. No. 4,909,964. The compounds of the present invention may be used in such a device.

A conventional nonlinear optical device disclosed in U.S. Pat. No. 4,909,964 comprises means to direct at least one incident beam of electromagnetic radiation into an element. The element has nonlinear optical properties whereby electromagnetic radiation emerging from the element contains at least one frequency different from the frequency of any incident beam of radiation. The different frequency is an even multiple of the frequency of one incident beam of electromagnetic radiation.

Preferably, the emerging radiation of a different frequency is doubled (second-order) (SHG). Preferably, the electromagnetic radiation is radiation from one of a number of common lasers, such as Nd-YAG, Raman-shifted Nd-YAG, Nd-YLF or Nd-glass, semiconductor diode, Er-Glass, Ti-Sapphire, dye, and Ar or Kr ion, or radiation shifted to other frequencies by nonlinear processes. For example, polarized light of wavelength 1.06 ,μm from an Nd-YAG laser is incident on the optical element along the optical path. A lens focuses the light into the optical element. Light emerging from the optical element is collimated by a similar lens and passed through a filter adapted to remove light of wavelength 1.06 μm while passing light of wavelength 0.53 ,μm.

As disclosed in U.S. Pat. No. 4,909,964 (incorporated herein by reference), one conventional electro-optic modulator comprises means to direct a coherent beam into an optical element, and means to apply an electric field to the element in a direction to modify the transmission property of the beam. For example, in an electro-optic modulator comprising an optical element, a pair of electrodes is attached to the upper and lower surfaces of the element, across which a modulating electric field is applied from a conventional voltage source. The optical element is placed between two polarizers. A light beam (such as that from a Nd-YAG laser) is polarized by a polarizer, focused on the optical element and propagated therethrough, and subjected to modulation by the electric field. The modulate light beam is led out through an analyzer polarizer. Linearly polarized light traversing the optical element is rendered elliptically polarized by action of the applied modulating voltage. The analyzer polarizer renders the polarization linear again. Application of the modulating voltage alters the birefringence of the optical element and consequently the ellipticity impressed on the beam. The analyzer polarizer then passes a greater or lesser fraction of the light beam as more or less of the elliptically polarized light projects onto its nonblocking polarization direction.

It will be further apparent to those skilled in the art that the optical elements formed by the poled polymers of the present invention are useful in this and other devices utilizing their nonlinear properties, such as devices utilizing the electro-optic effect.

One common form the optical element can take is that of a Langmuir-Blodgett (LB) film. A small amount of a compound useful in the practice of this invention spread on the surface of a liquid forms a surface film of monomolecular thickness at the air/liquid interface. If the supporting liquid is a polar liquid, such as water, the hydrophilic moieties of the compound are drawn into the liquid, while the hydrophobic moieties of the compound are attracted to the nonpolar, air side of the interface to hold the polar molecules at the surface of the supporting liquid body, resulting in polar alignment of the polar molecules on the surface of the supporting liquid. When the supporting substrate is slowly immersed in the film bearing liquid body or slowly withdrawn from it, an oriented monomolecular film is formed on the substrate.

The nonlinear optical device according to the invention comprises a means to direct at least one incident of electromagnetic radiation onto an optical element having nonlinear optical properties whereby electromagnetic radiation emerging from the element contains at least one frequency different from the frequency of any incident beam of radiation, the different frequency being an even multiple of the frequency of one incident beam of electromagnetic radiation. The optical element is selected from one of the forms described above. Preferably, the emerging radiation of a different frequency is doubled, i.e. SHG.

The optical element of the invention can also be utilized in an electrooptic modulator, wherein an electric field is applied to the optical element in a direction to modify the transmission properties of the element.

Compositions of matter which are covered by the present invention have the formula:

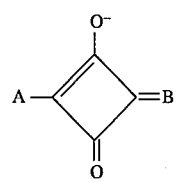

wherein A and B are different substituted compounds which give the squaraine unexpectedly large β.

A first group (Group I) of compounds in accordance with the present invention includes squaraines where

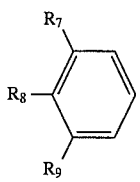

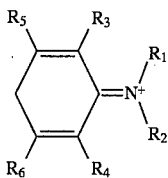

The general formula for Group I compounds is as follows:

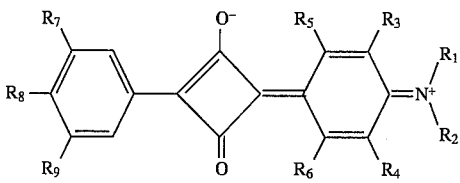

wherein $R_1$ is alkyl, $(CH_2)_nOH$ where n=1–8, $(CH_2)_nSH$ where n=1–8, phenylmethyl, 4-halophenylmethyl or $R_1+R_3=(CH_2)_3$; $R_2$ is alkyl, $(CH_2)_nOH$ where n=1–8, $(CH_2)_nSH$ where n=1–8, phenylmethyl, 4-halophenylmethyl or $R_2+R_4=(CH_2)_3$; $R_1$ and $R_2$ is a cyclic amine of the form $N(CH_2)_n$ where n=3–10; $R_3$ is H or $R_3+R_1=(CH_2)_3$; $R_4$ is H or $R_4+R_2=(CH_2)_3$; $R_5$ is H, F, OH, SH, $CH_3$, $C_2H_5$, $OCH_3$, or $SCH_3$; $R_6$ is H, F, OH, SH, $CH_3$, $C_2H_5$, $OCH_3$, or $SCH_3$; $R_7$ is H, alkyloxy or aryloxy; $R_8$ is H, alkyloxy or aryloxy; and $R_9$ is H, alkyloxy or aryloxy.

A second group (Group II) of compounds in accordance with the present invention includes squaraines wherein

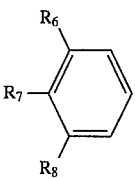

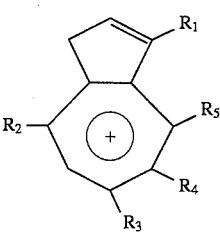

The formula for Group II compounds is as follows:

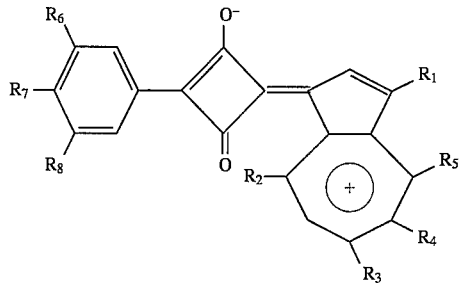

wherein $R_1$ is H or methyl; $R_2$ is H or methyl; $R_3$ is H or methyl; $R_4$ is H or isopropyl; $R_5$ is H or methyl; $R_6$ is H, alkyloxy or aryloxy; $R_7$ is H, $N(CH_3)_2$, alkyloxy or aryloxy; and $R_8$ is H, alkyloxy or aryloxy.

A third group (Group III) of compounds in accordance with the present invention includes squaraines wherein

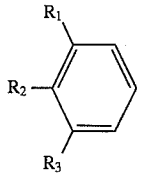

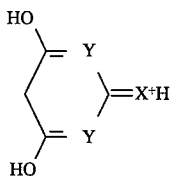

The general formula for Group III compounds is as follows:

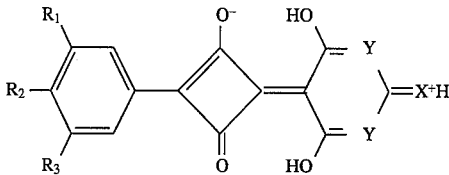

wherein X is O or S; Y is CH or N; $R_1$ is H, alkyloxy or aryloxy; $R_2$ is H, $N(CH_3)_2$, alkyloxy or aryloxy; and $R_3$ is H, alkyloxy or aryloxy.

A fourth group (Group IV) of compounds in accordance with the present invention includes squaraines wherein

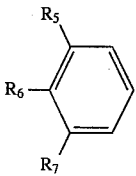

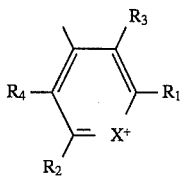

The formula for Group IV compounds is as follows:

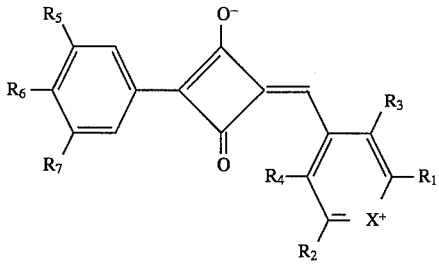

wherein X is NR where R=alkyl, $(CH_2)_nOH$ where n=1–8, or $(CH_2)_nSH$ where n=1–8, or where X is O, S, Se, or Te; $R_1$ and $R_2$ are H, tert-butyl, phenyl 4-toluyl; $R_3$ and $R_4$ are H or $R_1$ and $R_3$ is HC=CH—HC=CH and $R_2$ is phenyl, or $R_1$, $R_3$, $R_2$ and $R_4$ are HC=CH—HC=CH; $R_5$ is H, alkyloxy or aryloxy; $R_6$ is H, $N(CH_3)_2$, alkyloxy or aryloxy; and $R_7$ is H, alkyloxy or aryloxy.

A fifth group (Group V) of compounds in accordance with the present invention includes squaraines wherein

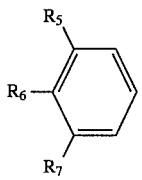

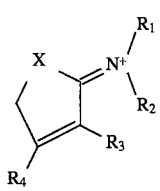

The formula for Group V compounds is as follows:

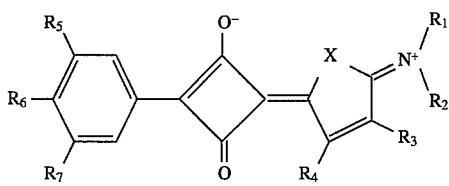

wherein $R_1$ and $R_2$ are $(CH_2)_2O(CH_2)_2$, $(CH_2)_4$, or $(CH_2)_5$; $R_3$ is H, phenyl, or 3-methoxyphenyl; $R_4$ is H, phenyl, 4-bromophenyl, or 2-chlorophenyl; $R_5$ is H, alkyloxy or aryloxy; $R_6$ is H, $N(CH_3)_2$, alkyloxy or aryloxy; $R_7$ is H, alkyloxy or aryloxy; and X is O, S, Se, or Te.

A sixth group (Group VI) of compounds in accordance with the present invention includes squaraines wherein

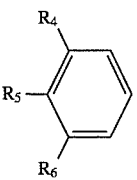

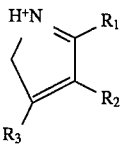

The formula for Group VI compounds is as follows:

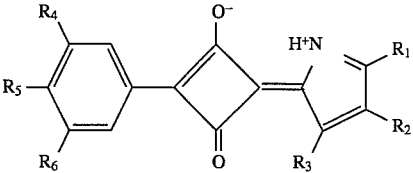

wherein $R_1$ is methyl, $R_2$ is H, alkyl, acetyl, or alkoxycarbonyl; $R_3$ is H or methyl; $R_4$ is H, alkyloxy or aryloxy; $R_5$ is H, $N(CH_3)_2$, alkyloxy or aryloxy; and $R_6$ is H, alkyloxy or aryloxy.

A seventh group (Group VII) of compounds in accordance with the present invention includes squaraines wherein

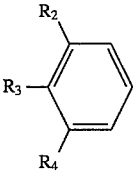

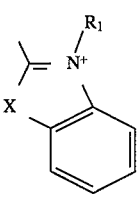

The formula for Group VII compounds is as follows:

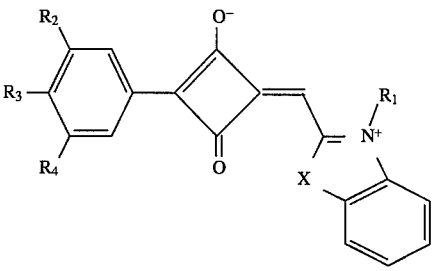

wherein $R_1$ is alkyl; X is HC=CH, $(CH_3)_2C$, O, S, Or Se; $R_2$ is H, alkyloxy or aryloxy; $R_3$ is H, $N(CH_3)_2$, alkyloxy or aryloxy; and R4 is H, alkyloxy or aryloxy.

An eighth group (Group VIII) of compounds in accordance with the present invention includes squaraines wherein

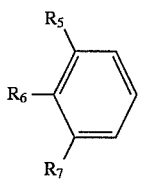

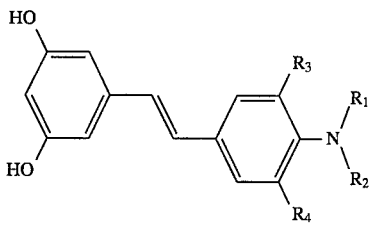

The formula for Group VIII compounds is as follows:

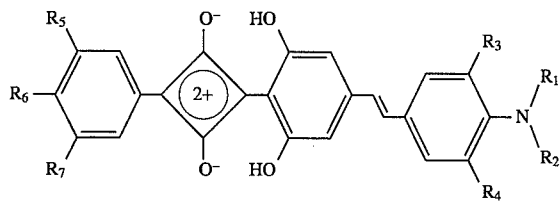

wherein $R_1$ is alkyl, $(CH_2)_nOH$ where n=1–8, $(CH_2)_nSH$ where n=1–8, phenylmethyl, 4-halophenylmethyl or $R_1+R_3=(CH_2)_3$; $R_2$ is alkyl, $(CH_2)_nOH$ where n=1–8, $(CH_2)_nSH$ where n=1–8, phenylmethyl, 4-halophenylmethyl or $R_2+R_4=(CH_2)_3$; $R_1$ and $R_2$ are a cyclic amine of the form $N(CH_2)_n$ where n=3–10; $R_3$ is H or $R_3+R_1=(CH_2)_3$; R4 is H or $R_4+R_2=(CH_2)_3$; $R_5$ is H, alkyloxy or aryloxy; $R_6$ is H, $N(CH_3)_2$, alkyloxy or aryloxy; and $R_7$ is H, alkyloxy or aryloxy.

A ninth group (Group IX) of compounds in accordance with the present invention includes squaraines wherein

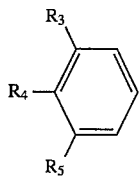

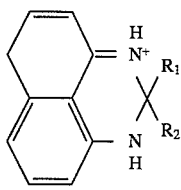

The formula for Group IX compounds is as follows:

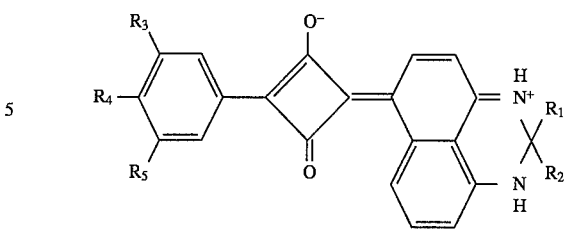

wherein $R_1$ is H, alkyl, $(CH_2)_nOH$ where n=1–8, $(CH_2)_nSH$ where n=1–8, phenylalkyl, phenyl, phenylcarbonyl, aryl, arylcarbonyl, arylalkyl, alkoxycarbonylalkyl, phenylcarbonylalkyl, or arylcarbonylalkyl.; $R_2$ is H, alkyl, $(CH_2)_nOH$ where n=1–8, $(CH_2)_nSH$ where n=1–8, phenylalkyl, phenyl, phenylcarbonyl, aryl, arylcarbonyl, arylalkyl, alkoxycarbonylalkyl, phenylcarbonylalkyl, or arylcarbonylalkyl.; $R_3$ is H, alkyloxy or aryloxy; $R_4$ is H, $N(CH_3)_2$, alkyloxy or aryloxy; and $R_5$ is H, alkyloxy or aryloxy.

Alkyl groups set forth in the above formulas include those groups having up to 10 carbon atoms and includes both branched and straight chain alkyl groups. Exemplary alkyl groups include methyl, ethyl, propyl, butyl, pentyl, hexyl, heptyl, octyl, nonyl, in the normal, secondary, iso and neo attachment isomers. Aryl groups referred to in the preceding formulas include aromatic hydrocarbons having up to 10 carbon atoms. Exemplary aryl groups include phenyl, naphthyl, furanyl, thiophenyl, pyrrolyl, selenophenyl, tellurophenyl.

Figure 2:
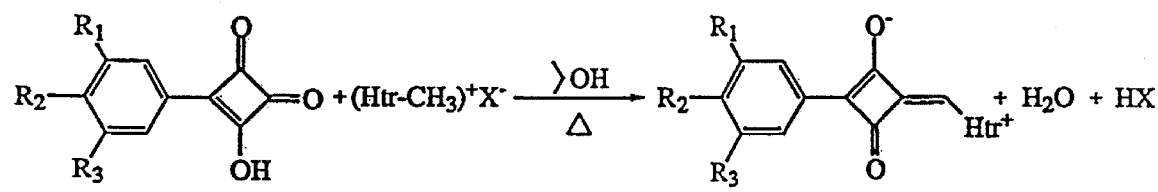
FIG. 2 is a schematic representation of the synthesis of an exemplary composition wherein $(Htr-CH_3)^+X^-$ is an ionic donor.

The compositions of the present invention are prepared by condensing monosubstituted squaric acid precursors, 1-(alkoxyphenyl)-2-hydroxycyclobutene-3,4-dione, with an appropriate donors as D-H or under similar conditions described by Law and Bailey (J. Org. Chem. 1992, 57, 3278). As schematically shown in FIG. 1 for the exemplary case where D-H is 4-N,N-dibutylamino-3'5'-dihydroxystilbene. FIG. 2 is a schematic representation of the synthesis where $(Htr-CH_3)^+X^-$ is N-butyllepidinum iodide In both FIG. 1 and 2 the monosubstituted squaric acid precursors is 1-(4-isopentyloxyphenyl)-2-hydroxycyclobutene-2,4-dione and 1-(4-methoxyphenyl)-2-hydroxycyclobutene-2,4-dione, respectively.

A compound in accordance with the present invention was prepared where monosubstituted squaric acid precursors was 1-(4-isopentyloxyphenyl)-2-hydroxycyclobutene-2,4-dione and $(Htr-CH_3)^+X^-$ was 1,2-dimethylbenzothiazolium p-toluenesulfonate. The procedure which was used to prepare this composition was as follows:

Preparation of the product is carried out by mixing 1-(4-isopentyloxyphenyl)-2-hydroxycyciobutene-2,4-dione (1.153 mmole) and 1,2-dimethylbenzothiazolium p-toluenesulfonate (1.153 mmole) in a 25 mL round-bottom flask containing a magnetic stir bar, dry iso-propanol (8 mL) and tributylorthoformate (1 mL) were then added to the flask. The flask with the mixture was blown with argon for a few minutes and then charged with a water-cooling condenser with the inlet and outlet for argon flow. The solution was brought to refluxing under argon for 1.5 hours. During the refluxing, the color of the solution changed from pale orange-yellow to orange and eventually dark red-orange. Accompanying the color change, a burgundy fiber-like crystalline solid with metallic sheen was developing. After the solution was cooled to room temperature for 18 hours, the solution was filtered through a course glass frit. The burgundy crystalline solid isolated was washed with isopropanol (5 mL), diethyl ether (10 mL) and then air dry. The yield is 0.41 gm (0.992 mmole, 86%). The burgundy fluffy fiber-like solid is analytically pure. For other unsymmetrical squaraine molecules, sometimes a further recrystallization has to be performed in order to obtain analytically pure sample. The solvents for the recrystallization are chloroform for molecules synthesized from D-H and pyridine/hexanes for those synthesized from $(Htr-CH_3)^+X^-$.

A number of exemplary compositions in accordance with the present invention were prepared following the above-described procedure. The results of NMR analysis for the various compositions are as follows:

EXAMPLE 1

Group I $R_1=R_2=$ethyl $R_3=R_4=R_6=R_7=R_9=$H $R_5=$OH $R_8=$iso-pentyloxy $^1$H NMR (CDCl$_3$): δ 13.56 (bs, 1H), 8.2 (d, J=8.9 Hz, 2H), 8.11 (d, J=9.3 Hz, 1H), 6.97 (d, J=8.9 Hz, 2H), 6.44 (dd, $J_A$=9.3 Hz, $J_B$=2.4 Hz, 1H), 6.12 (d, J=2.4 Hz, 1H), 4.07 (t, J=6.6 Hz, 2H), 3.54 (q, J=6.6 Hz, 2H), 1.85 (m, 1H), 1.70 (m, 2H), 1.30 (t, J=7.2 Hz, 6H), 0.96 (d, J=6.6 Hz, 6H). $^{13}$C{$^1$H} NMR (CDCl$_3$): δ 187.8, 184.4, 180.8, 170.5, 168.2, 162.9, 159.3, 134.5, 131.1, 130.8, 123.8, 120.5, 115.2, 113.0, 109.7, 98.2, 66.7, 46.0, 37.8, 25.0, 22.5, 13.1. FAB-MS: calc'd MW, 407.49, m/e=407. Anal. Calc'd for C$_{25}$H$_{29}$NO$_4$: C, 73.68; H, 7.17; N, 3.44. Found: C, 73.58; H, 7.20; N, 3.41. UV-vis (in CHCl$_3$), $\lambda_{max}$,nm (ε, 10$^4$ M$^{-1}$cm$^{-1}$): 570 (14).

EXAMPLE 2

Group I $R_1+R_3=R_2+R_4=(CH_2)_2$ $R_6=R_7=R_9=$H $R_5=$OH $R_8=$iso-pentyloxy $^1$H NMR (CDCl$_3$): δ 13.50 (bs, 1H), 8.14 (d, J=8.9 Hz, 2H), 7.69 (s, 1H), 6.95 (d, J=8.9 Hz, 2H), 4.05 (t, J=6.6 Hz, 2H), 3.40 (bt, 4H), 2.70 (bt, J=6.0 Hz, 4H), 1.83 (m, 1H), 1.95 (m, 4H), 1.69 (m, 2H), 0.97 (d, J=6.6 Hz, 6H). $^{13}$C{$^1$H} NMR (CDCl$_3$): δ 184.7, 183.8, 181.7, 164.6, 162.5, 161.7, 155.6, 129.9, 129.0, 124.1, 119.9, 115.0, 113.3, 107.0, 66.6, 51.6, 51.2, 37.8, 26.7, 25.0, 22.6, 21.3, 20.0, 19.6. FAB-MS: calc'd MW, 431.51, m/e=431. Anal. Calc'd for C$_{27}$H$_{29}$NO$_4$: C, 75.15 H, 6.77; N, 3.25. Found: C, 74.47; H, 6.80; N, 3.24. UV-vis (in CHCl$_3$), $\lambda_{max}$,nm (ε, 10$^4$ M$^{-1}$cm$^{-1}$): 572 (9).

EXAMPLE 3

Group I $R_1=R_2=$methyl $R_3=R_4=R_6=R_7=R_9=$H $R_5=$methyl $R_8=$methoxy $^1$H NMR (CDCl$_3$): δ 9.10 (d, J = 9.3 Hz, 1H), 8.45 (d, J=9.0 Hz, 2H), 7.01 (d, J=9.0 Hz, 2H), 6.65 (dd, $J_A$=9.3 Hz, $J_B$=2.7 Hz, 1H), 6.61 (d, J=2.7 Hz, 1H), 3.91 (s, 3H), 3.27 (s, 6H), 2.95 (s, 3H). FAB-MS: calc'd MW, 321.36, m/e= 322. Anal. Calc'd for C$_{20}$H$_{19}$NO$_3$: C, 74.75 H, 5.96; N, 4.36. Found: C, 74.74; H, 5.97; N, 4.30. UV-vis (in CHCl$_3$), $\lambda_{max}$,nm (ε, 10$^4$ M$^{-1}$cm$^{-1}$): 584 (22).

EXAMPLE 4

Group I $R_1=R_2=$methyl $R_3=R_4=R_5=R_6=R_7=R_9=$H $R_8=$methoxy $^1$H NMR (CDCl$_3$): δ 8.49 (d, J=9.3 Hz, 2H), 8.43 (d, J=8.9 Hz, 2H), 7.01 (d, J=8.9 Hz, 2H), 6.82 (d, J=9.3 Hz, 2H), 3.92 (s, 3H), 3.28 (s, 6H). FAB-M S: calc'd MW, 307.33, m/e=307. Anal. Calc'd for C$_{19}$H$_{17}$NO$_3$: C, 74.25 H, 5.58; N, 4.56. Found: C, 73.98; H, 5.63; N, 4.47. UV-vis (in CHCl$_3$), $\lambda_{max}$,nm (ε, 10$^4$ M$^{-1}$cm$^{-1}$): 580 (23).

EXAMPLE 5

Group II $R_1=R_2=$methyl $R_3=R_5$ $R_4=$iso-propyl $R_6=R_8=$H $R_7=$iso-pentyloxy $^1$H NMR (CDCl$_3$): δ 8.95 (s, 1H), 8.41 (d, J=8.7 Hz, 2H), 8.19 (s, 1H), 7.77 (m, 2H), 6.98 (d, J=8.7 Hz, 2H), 4.09 (t, J=6.6 Hz, 2H), 3.50 (s, 3H), 3.21 (hep, J=6.8 Hz, 1H), 2.52 (s, 3H), 1.84 (m, 1H), 1.71 (m, 2H), 1.41 (d, J=6.8 Hz, 6H), 0.98 (d, J=6.6 Hz, 6H). FAB-MS: calc'd MW, 440.55, m/e=441. Anal. Calc'd for C$_{30}$H$_{32}$O$_3$: C, 81.78 H, 7.32. Found: C, 81.68; H, 7.40. UV-vis (in CHCl$_3$), $\lambda_{max}$,nm (ε, 10$^4$ M$^{-1}$cm$^{-1}$): 644 (9.8).

EXAMPLE 6

Group III $R_1=R_3=$H $R_2=$iso-pentyloxy

X=O

Y=N $^1$H NMR (d$_7$-DMF): δ 11.84 (bs, 2H), 8.02 (d, J=8.7 Hz, 2H), 7.24 (d, J=8.7 Hz, 2H), 4.20 (t, J=6.5 Hz, 2H), 1.82 (m, 1H), 1.70 (m, 2H), 0.97 (d, J=6.6 Hz, 6H). FAB-MS: calc'd MW, 370.35, m/e=371. Anal. Calc'd for C$_{19}$H$_{18}$N$_2$O$_6$: C, 61.62; H, 4.90; N, 7.56. Found: C, 61.73; H, 4.94; N, 7.60. UV-vis (in DMF), $\lambda_{max}$,nm (ε, 10$^4$ M$^{-1}$cm$^{-1}$): 484 (in CHCl$_3$) 470 (4.9).

EXAMPLE 7

Group III $R_1=R_3=$H $R_2=$iso-pentyloxy

X=S

Y=N $^1$H NMR (d$_7$-DMF): δ 12.97 (bs, 2H), 8.05 (d, J=8.7 Hz, 2H), 7.26 (d, J=8.7 Hz, 2H), 4.21 (t, J=6.6 Hz, 2H), 1.82 (m, 1H), 1.70 (m, 2H), 0.97 (d, J=6.6 Hz, 6H). FAB-MS: calc'd MW, 386.41, m/e=387. Anal. Calc'd for C$_{19}$H$_{18}$N$_2$O$_5$S: C, 59.05; H, 4.70; N, 7.25; S, 8.3. Found: C, 59.06; H, 4.70; N, 7.28; S, 8.22. UV-vis (in CHCl$_3$), $\lambda_{max}$,nm (ε, 10$^4$ M$^{-1}$cm$^{-1}$): 504 (5.2).

EXAMPLE 8

Group IV
$R_1+R_3=(HC=CH-HC=CH)$
$R_2=R_4=R_5=R_7=H$
$R_6$=iso-pentyloxy
$X=N(CH_2)_3CH_3$ $^1$H NMR (CDCl$_3$): δ 9.66 (d, J=6.9 Hz, 1H), 9.07 (d, J=6.9 Hz, 1H), 8.80 (d, J=8.4 Hz, 1H), 8.47 (d, J=8.7 Hz, 1H), 8.16 (t, J=7.5 Hz, 1H), 8.10 (d, J=8.7 Hz, 2H), 7.94 (t, J=7.5 Hz, 1H), 7.03 (d, J=8.7 Hz, 2H), 6.96 (s, 1H), 4.93 (t, J=7.5 Hz, 2H), 3.86 (s, 3H), 2.04 (m, 2H), 1.50 (m, 2H), 0.98 (t, J=7.2 Hz, 3H). FAB-MS: calc'd MW, 385.44, m/e=386. Anal. Calc'd for C$_{25}$H$_{23}$NO$_3$: C, 77.90; H, 6.01; N, 3.63. Found: C, 77.34; H, 5.98; N, 3.85. UV-vis (in CHCl$_3$), λ$_{max}$,nm (ε, 10$^4$ M$^{-1}$cm$^{-1}$): 616 (14).

EXAMPLE 9

Group VII
$R_1$=methyl
$R_2=R_4$=H
$R_3$=iso-pentyloxy
X=(HC=CH)

$^1$H NMR (d$_7$-DMF): δ 9.73 (d, J=9.0 Hz, 1H), 8.67 (d, J=9.0 Hz, 1H), 8.42 (d, J=9.0 Hz, 1H), 8.21 (d, J=7.2 Hz, 1H), 8.10 (d, J=8.7 Hz, 2H), 8.05 (t, J=7.1 Hz, 1H), 7.81 (t, J=7.1 Hz, 1H), 7.06 (d, J=8.7 Hz, 2H), 6.55 (s, 1H), 4.49 (s, 3H), 4.11 (t, J = 6.6 Hz, 2H), 1.83(m, 1H), 1.67(m, 2H), 0.97 (d, J=6.3 Hz, 6H). FAB-MS: calc'd MW, 399.47, m/e=400. Anal. Calc'd for C$_{26}$H$_{25}$NO$_3$: C, 77.49; H, 6.50; N, 3.62. Found: C, 77.85; H, 6.43; N, 3.62. UV-vis (in CHCl$_3$), λ$_{max}$,nm (ε, 10$^4$ M$^{-1}$cm$^{-1}$): 576 (6).

EXAMPLE 10

Group VII
$R_1$=ethyl
$R_2=R_4$=H
$R_3$=iso-pentyloxy
X=(HC=CH)

$^1$H NMR (d$_7$-DMF): δ 9.79 (d, J=9.0 Hz, 1H), 8.68 (d, J=9.0 Hz, 1H), 8.45 (d, J=9.0 Hz, 1H), 8.22 (d, J=7.5 Hz, 1H), 8.11 (d, J=8.7 Hz, 2H), 8.07 (t, J=7.5, 1H), 7.82 (t, J=7.5 Hz, 1H), 7.07 (d, J=8.7 Hz, 2H), 6.51 (s, 1H), 5.03 (q, J=6.5 Hz, 2H), 4.11 (t, J=6.9 Hz, 3H), 1.82 (m, 1H), 1.68 (m, 2H), 0.97 (d, J=6.6 Hz, 6H). FAB-MS: calc'd MW, 413.49, m/e=414. Anal. Calc'd for C$_{27}$H$_{27}$NO$_3$: C, 78.42; H, 6.58; N, 3.39. Found: C, 78.34; H, 6.61; N, 3.42. UV-vis (in CHCl$_3$), λ$_{max}$,nm (ε, 10$^4$ M$^{-1}$cm$^{-1}$): 572 (6).

EXAMPLE 11

Group VII
$R_1$=methyl
$R_2=R_4$=H
$R_3$=methoxy
$X=(CH_3)_2C$ $^1$H NMR (d$_7$-DMF): δ 8.21 (d, J=8.9 Hz, 2H), 7.79 (d, J=6.0 Hz, 1H), 7.81 (d, J=7.5 Hz, 1H), 7.58 (t, J=7.5 Hz, 1H), 7.51 (t, J=7.4 Hz, 1H), 7.11 (d, J=8.9 Hz, 2H), 6.34 (s, 1H), 4.06 (s, 3H), 3.90 (s, 3H), 1.85 (s, 6H). FAB-MS: calc'd MW, 359.41, m/e=360. Anal. Calc'd for C$_{23}$H$_{21}$NO$_3$: C, 76.86; H, 5.89; N, 3.90. Found: C, 76.76; H, 5.92; N, 3.94. UV-vis (in CHCl$_3$), λ$_{max}$,nm (ε, 10$^4$ M$^{-1}$cm$^{-1}$): 556 (11).

EXAMPLE 12

Group VII
$R_1$=ethyl
$R_2=R_4$=H
$R_3$=methoxy
X=O $^1$H NMR (d$_7$-DMF): δ 8.16 (d, J=9.0 Hz, 2H), 8.05–8.08 (m, 1H), 7.99–8.03 (m, 1H), 7.66–7.70 (m, 2H), 7.08 (d, J=9.0 Hz, 2H), 6.32 (s, 1H), 4.74 (q, J=7.2 Hz, 2H), 3.88 (s, 3H), 1.58 (t, J=7.2 Hz, 3H). FAB-MS: calc'd MW, 347.35, m/e=348. Anal. Calc'd for C$_{21}$H$_{17}$NO$_4$: C, 72.61; H, 4.03; N, 3.90. Found: C, 70.92; H, 5.06; N, 3.95. UV-vis (in CHCl$_3$), λ$_{max}$,nm (ε, 10$^4$ M$^{-1}$cm$^{-1}$): 518 (10).

EXAMPLE 13

Group VII
$R_1$=methyl
$R_2=R_4$=H
$R_3$=iso-pentyloxy
X=S $^1$H NMR (d$_7$-DMF): δ 8.33 (d, J=7.8 Hz, 1H), 8.13 (d, J=7.8 Hz, 1H), 8.09 (d, J=9.0 Hz, 2H), 7.78 (t, J=7.7 Hz, 1H), 7.67 (t, J=7.5 Hz, 1H), 7.06 (d, J=9.0 Hz, 2H), 6.58 (s, 1H), 4.30 (s, 3H), 4.11 (t, J=6.6 Hz, 2H), 1.82 (m, 1H), 1.67 (m, 2H), 0.96 (d, J=6.6 Hz, 6H). FAB-MS: calc'd MW, 347.35, m/e=348. Anal. Calc'd for C$_{24}$H$_{23}$NO$_3$S: C, 71.08; H, 5.72; N, 3.46; S, 7.91. Found: C, 71.20; H, 5.73; N, 3.51; S, 7.83. UV-vis (in CHCl$_3$), λ$_{max}$,nm (ε, 10$^4$ M$^{-1}$cm$^{-1}$): 554 (10).

EXAMPLE 14

Group VII
$R_1$=ethyl
$R_2=R_4$=H
$R_3$=iso-pentyloxy
X=Se $^1$H NMR (d$_7$-DMF): δ 8.39 (d, J=7.8 Hz, 1H), 8.11 (d, J=7.5 Hz, 1H), 8.08 (d, J=8.7 Hz, 2H), 7.73 (t, J=7.8 Hz, 1H), 7.58 (t, J=7.5 Hz, 1H), 7.06 (d, J=8.7 Hz, 2H), 6.68 (s, 1H), 4.85 (q, J=7.1 Hz, 2H), 4.11 (t, J=6.6 Hz, 2H), 1.82 (m, 1H), 1.67 (m, 2H), 1.53 (t, J=7.1 Hz, 3H), 0.96 (d, J=6.6 Hz, 6H). FAB-MS: calc'd MW, 466.44, m/e=468. Anal. Calc'd for C$_{25}$H$_{25}$NO$_3$Se: C, 64.37; H, 5.40; N, 3.00. Found: C, 64.44; H, 5.41; N, 3.01. UV-vis (in CHCl$_3$), λ$_{max}$,nm (ε, 10$^4$ M$^{-1}$cm$^{-1}$): 562 (10).

EXAMPLE 15

Group VIII
$R_1=R_2$=butyl
$R_3=R_4=R_5=R_7$=H
$R_6$=iso-pentyloxy $^1$H NMR (CDCl$_3$): δ 12.80 (s, 2H), 8.24 (d, J=8.9 Hz, 2H), 7.45 (d, J=8.7 Hz, 2H), 7.41 (d, J=16.0 Hz, 1H), 7.02 (d, J=8.9 Hz, 2H), 6.74 (d, J=16.0 Hz, 1H), 6.63 (d, J=8.7 Hz, 2H), 6.47 (s, 2H), 4.12 (t, J=6.6 Hz, 2H), 1.83 (m, 1H), 1.72 (m, 2H), 1.58 (m, 2H), 1.37 (m, 2H), 0.97 (t, J=6.9 Hz, 6H). $^{13}$C{$^1$H} NMR (CDCl$_3$): δ 182.5, 165.3, 150.0, 139.8, 132.4, 130.5, 121.8, 122.9, 115.9, 111.7, 108.9, 106.5, 98.9, 67.1, 50.8, 37.6, 29.5, 25.0, 22.5, 20.3, 13.9. FAB-MS: calc'd MW, 581.72, m/e=583. Anal. Calc'd for $C_{37}H_{43}NO_5 \cdot H_2O$: C, 74.09; H, 7.56; N, 2.34. Found: C, 74.29; H, 7.55; N, 2.34. UV-vis (in $CHCl_3$), $\lambda_{max}$,nm (s, $10^4$ $M^{-1}cm^{-1}$): 732 (6).

Fifteen different compounds produced by the above-described procedure were analyzed to determine first molecular hyperpolarizabilities. The results of these determinations are set forth in Tables 1–6. Tables 1–5 show the measured β for the sixteen exemplary compounds in accordance with the present invention. Table 6 sets forth measurements for compounds not covered by the present invention.

TABLE 1

| General formula I | $\mu \times 10^{18}$ (esu) | $\beta \times 10^{30}$ (esu) | $\beta_{(0)} \times 10^{30}$ (esu) | $\mu\beta \times 10^{48}$ (esu) |
|---|---|---|---|---|
| $R_1 = R_2$ = ethyl<br>$R_{3,4,6,7,9}$ = H<br>$R_5$ = OH<br>$R_8$ = iso-pentyloxy | 6.5 | −53 | −31 | −345 |
| $R_1 + R_3 = R_2 + R_4 = (CH_2)_3$<br>$R_5$ = OH<br>$R_{6,7,9}$ = H<br>$R_8$ = iso-pentyloxy | 7.4 | −62 | −36 | −459 |

TABLE 2

| General formula II | $\mu \times 10^{18}$ (esu) | $\beta \times 10^{30}$ (esu) | $\beta_{(0)} \times 10^{30}$ (esu) | $\mu\beta \times 10^{48}$ (esu) |
|---|---|---|---|---|
| $R_{1,2}$ = methyl<br>$R_{3,5,6,8}$ = H<br>$R_4$ = iso-propyl<br>$R_7$ = iso-pentyloxy | 6.5 | −53 | −31 | −345 |

TABLE 3

| General formula IV | $\mu \times 10^{18}$ (esu) | $\beta \times 10^{30}$ (esu) | $\beta_{(0)} \times 10^{30}$ (esu) | $\mu\beta \times 10^{48}$ (esu) |
|---|---|---|---|---|
| $R_1\ R_3$ =<br>HC=CH—HC=CH<br>$R_{2,4,5,7}$ = H<br>$R_6$ = iso-pentyloxy<br>X = $N(CH_2)_3CH_3$ | 8.5 | −120 | −63 | −1020 |

TABLE 4

![Structure VII]

| General formula VII | $\mu \times 10^{18}$ (esu) | $\beta \times 10^{30}$ (esu) | $\beta_{(0)} \times 10^{30}$ (esu) | $\mu\beta \times 10^{48}$ (esu) |
|---|---|---|---|---|
| $R_1$ = methyl<br>$R_{2,4}$ = H<br>$R_3$ = iso-pentyloxy<br>X = (HC=CH) | 5.7 | −64 | −31 | −365 |
| $R_1$ = methyl<br>$R_{2,4}$ = H<br>$R_3$ = iso-pentyloxy<br>X = (HC=CH) | 7.5 | −94 | −55 | −473 |
| $R_1$ = methyl<br>$R_{2,4}$ = H<br>$R_3$ = methoxy<br>X = $(CH_3)_2$C | 7.5 | −69 | −42 | −518 |
| $R_1$ = ethyl<br>$R_{2,4}$ = H<br>$R_3$ = methoxy<br>X = O | 7.5 | −42 | −27 | −315 |
| $R_1$ = methyl<br>$R_{2,4}$ = H<br>$R_3$ = iso-pentyloxy<br>X = S | 7.7 | −95 | −58 | −732 |
| $R_1$ = ethyl<br>$R_{2,4}$ = H<br>$R_3$ = iso-pentyloxy<br>X = Se | 6.6 | −41 | −24 | −271 |

TABLE 5

![Structure VIII]

| General formula VIII | $\mu \times 10^{18}$ (esu) | $\beta \times 10^{30}$ (esu) | $\beta_{(0)} \times 10^{30}$ (esu) | $\mu\beta \times 10^{48}$ (esu) |
|---|---|---|---|---|
| $R_{1,2}$ = butyl<br>$R_{3,4,5,7}$ = H<br>$R_6$ = iso-pentyloxy | 8.1 | +481 | +170 | +3900 |

TABLE 6

![Structure]

| General Formula | $\mu \times 10^{18}$ (esu) | $\beta \times 10^{30}$ (esu) | $\beta_{(0)} \times 10^{30}$ (esu) | $\mu\beta \times 10^{48}$ (esu) |
|---|---|---|---|---|
| $R_{1,2}$ = methyl<br>$R_{3,4}$ = H<br>X = $NO_2$ | 6.6 | +73 | +55 | +482 |
| $R_1 + R_3$ = $(CH_2)_3$<br>$R_2 + R_4$ = $(CH_2)_3$<br>X = $NO_2$ | 7.0 | +96 | +72 | +672 |

As can be seen from the above Tables, compounds in accordance with the present invention (Table 1–5) have either positive or negative first molecular hyperpolarizabilities (β) in comparison with the compound set forth in Table 6. For example, the results in Table 5 show that this exemplary composition in accordance with the present invention has a β (0) of 170×10⁻³⁰ esu (after correcting for dispersion with a two state model). This is to be compared with the compounds in Table 6 which have β (0) of 55 and 72×10⁻³⁰ esu, respectively.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A composition of matter having the formula:

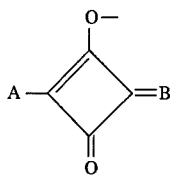

wherein A and B are selected from the group consisting of:

A is

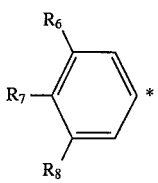

and B is

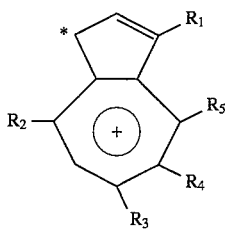

wherein * is the point of attachment, $R_1$ is H or methyl; $R_2$ is H or methyl; $R_3$ is H or methyl; $R_4$ is H or isopropyl; $R_5$ is H or methyl; $R_6$ is H, alkyloxy or aryloxy; $R_7$ is H, $N(CH_3)_2$, alkyloxy or aryloxy; and $R_8$ is H, alkyloxy or aryloxy;

A is

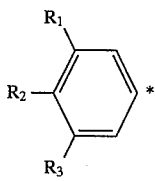

and B is

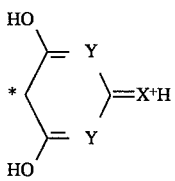

wherein * is the point of attachment, X is O or S; Y is CH or N; $R_1$ is H, alkyloxy or aryloxy; $R_2$ is H, $N(CH_3)_2$, alkyloxy or aryloxy; and $R_3$ is H, alkyloxy or aryloxy;

A is

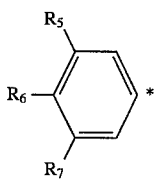

and B is

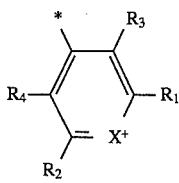

wherein * is the point of attachment, X is NR where R=alkyl, $(CH_2)_nOH$ where n=1–8, or $(CH_2)_nSH$ where n=1–8, or where X is O, S, Se, or Te; $R_1$ and $R_2$ are H, tert-butyl, phenyl 4-toluyl; $R_3$ and $R_4$ are H or $R_1$ and $R_3$ is HC=CH—HC=CH and $R_2$ is phenyl, or $R_1$, $R_3$, $R_2$ and $R_4$ are HC=CH—HC=CH; $R_5$ is H, alkyloxy or aryloxy; $R_6$ is H, $N(CH_3)_2$, alkyloxy or aryloxy; and $R_7$ is H, alkyloxy or aryloxy;

A is

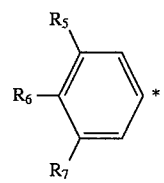

and B is

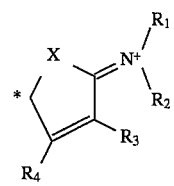

wherein * is the point of attachment, $R_1$ and $R_2$ are $(CH_2)_2O(CH_2)_2$, $(CH_2)_4$, or $(CH_2)_5$; $R_3$ is H, phenyl, or 3-methoxyphenyl; $R_4$ is H, phenyl, 4-bromophenyl, or 2-chlorophenyl; $R_5$ is H, alkyloxy or aryloxy; $R_6$ is H, $N(CH_3)_2$, alkyloxy or aryloxy; $R_7$ is H, alkyloxy or aryloxy; and X is O, S, Se, or Te;

A is

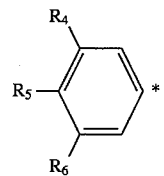

and B is

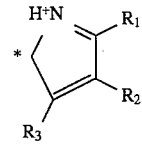

wherein * is the point of attachment, $R_1$ is methyl, $R_2$ is H, alkyl, acetyl, or alkoxycarbonyl; $R_3$ is H or methyl; $R_4$ is H, alkyloxy or aryloxy; $R_5$ is H, $N(CH_3)_2$, alkyloxy or aryloxy; and $R_6$ is H, alkyloxy or aryloxy;

A is

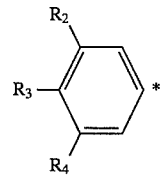

and B is

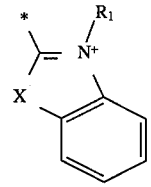

wherein * is the point of attachment, $R_1$ is alkyl; X is HC=CH, $(CH_3)_2C$, O, S, or Se; $R_2$ is H, alkyloxy or aryloxy;

$R_3$ is H, $N(CH_3)_2$, alkyloxy or aryloxy; and $R_4$ is H, alkyloxy or aryloxy;

A is

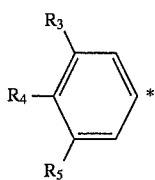

and B is

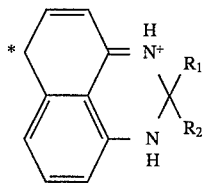

wherein * is the point of attachment, $R_1$ is H, alkyl, $(CH_2)_nOH$ where n=1–8, $(CH_2)_nSH$ where n=1–8, phenylalkyl, phenyl, phenylcarbonyl, aryl, arylcarbonyl, arylalkyl, alkoxycarbonylalkyl, phenylcarbonylalkyl, or arylcarbonylalkyl.; $R_2$ is H, alkyl, $(CH_2)_nOH$ where n=1–8, $(CH_2)_nSH$ where n=1–8, phenylalkyl, phenyl, phenylcarbonyl, aryl, arylcarbonyl, arylalkyl, alkoxycarbonylalkyl, phenylcarbonylalkyl, or arylcarbonylalkyl.; $R_3$ is H, alkyloxy or aryloxy; $R_4$ is H, $N(CH_3)_2$, alkyloxy or aryloxy; and $R_5$ is H, alkyloxy or aryloxy.

2. A composition of matter according to claim 1 having the formula:

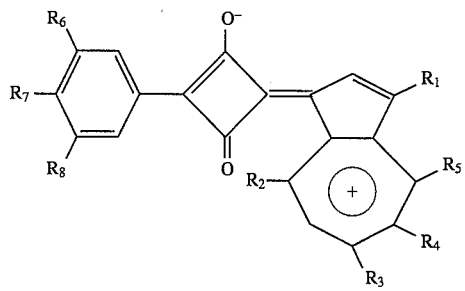

wherein $R_1$ is H or methyl; $R_2$ is H or methyl; $R_3$ is H or methyl; $R_4$ is H or isopropyl; $R_5$ is H or methyl; $R_6$ is H, alkyloxy or aryloxy; $R_7$ is H, $N(CH_3)_2$, alkyloxy or aryloxy; and $R_8$ is H, alkyloxy or aryloxy.

3. A composition of matter according to claim 1 having the formula:

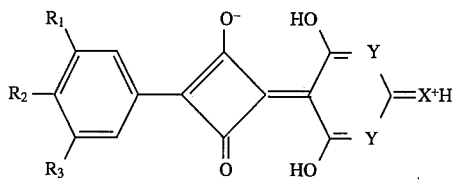

wherein X is O or S; Y is CH or N; $R_1$ is H, alkyloxy or aryloxy; $R_2$ is H, $N(CH_3)_2$, alkyloxy or aryloxy; and $R_3$ is H, alkyloxy or aryloxy.

4. A composition of matter according to claim 1 having the formula:

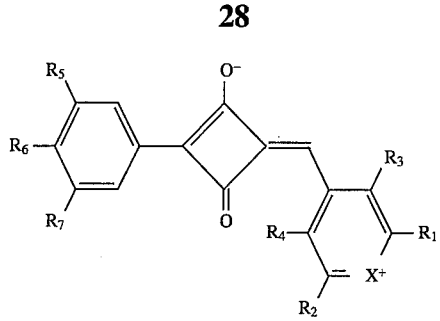

wherein X is NR where R=alkyl, $(CH_2)_nOH$ where n=1–8, or $(CH_2)_nSH$ where n=1–8, or where X is O, S, Se, or Te; $R_1$ and $R_2$ are H, tert-butyl, phenyl 4-toluyl; $R_3$ and $R_4$ are H or $R_1$ and $R_3$ is HC=CH—HC=CH and $R_2$ is phenyl, or $R_1$, $R_3$, $R_2$ and $R_4$ are HC=CH—HC=CH; $R_5$ is Fl, alkyloxy or aryloxy; $R_6$ is H, $N(CH_3)_2$, alkyloxy or aryloxy; and $R_7$ is H, alkyloxy or aryloxy.

5. A composition of matter according to claim 1 having the formula:

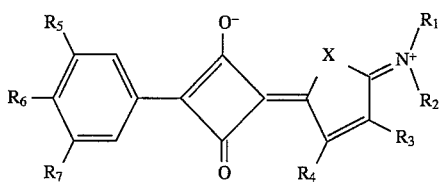

wherein $R_1$ and $R_2$ are $(CH_2)_2O(CH_2)_2$, $(CH_2)_4$, or $(CH_2)_5$; $R_3$ is H, phenyl, or 3-methoxyphenyl; $R_4$ is H, phenyl, 4-bromophenyl, or 2-chlorophenyl; $R_5$ is H, alkyloxy or aryloxy; $R_6$ is H, $N(CH_3)_2$, alkyloxy or aryloxy; $R_7$ is H, alkyloxy or aryloxy; and X is O, S, Se, or Te.

6. A composition of matter according to claim 1 having the formula:

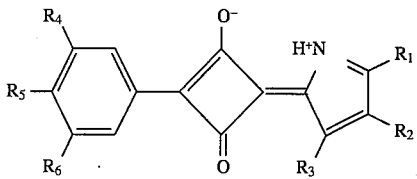

wherein $R_1$ is methyl, $R_2$ is H, alkyl, acetyl, or alkoxycarbonyl; $R_3$ is H or methyl; $R_4$ is H, alkyloxy or aryloxy; $R_5$ is H, $N(CH_3)_2$, alkyloxy or aryloxy; and $R_6$ is H, alkyloxy or aryloxy.

7. A composition of matter according to claim 1 having the formula:

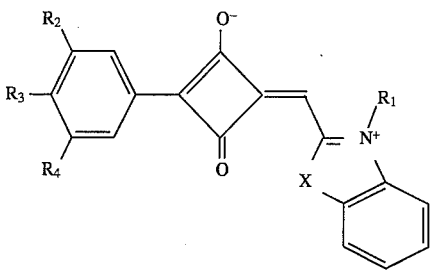

wherein $R_1$ is alkyl; X is HC=CH, $(CH_3)_2C$, O, S, or Se; $R_2$ is H, alkyloxy or aryloxy; $R_3$ is H, $N(CH_3)_2$, alkyloxy or aryloxy; and $R_4$ is H, alkyloxy or aryloxy.

8. A composition of matter according to claim 1 having the formula:

wherein R₁ is H, alkyl, $(CH_2)_nOH$ where n=1–8, $(CH_2)_nSH$ where n=1–8, phenylalkyl, phenyl, phenylcarbonyl, aryl, arylcarbonyl, arylalkyl, alkoxycarbonylalkyl, phenylcarbonylalkyl, or arylcarbonylalkyl.; R₂ is H, alkyl, $(CH_2)_nOH$ where n=1–8, $(CH_2)_nSH$ where n=1–8, phenylalkyl, phenyl, phenylcarbonyl, aryl, arylcarbonyl, arylalkyl, alkoxycarbonylalkyl, phenylcarbonylalkyl, or arylcarbonylalkyl.; R₃ is H, alkyloxy or aryloxy; R₄ is H, $N(CH_3)_2$, alkyloxy or aryloxy; and R₅ is H, alkyloxy or aryloxy.

9. A composition of matter having the formula:

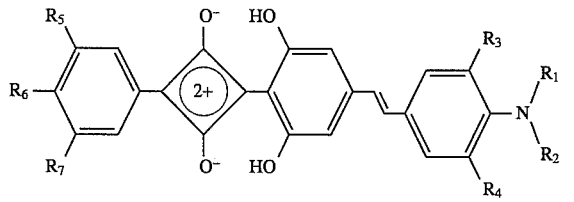

wherein R₁ is alkyl,$(CH_2)_nOH$ where n=1–8, $(CH_2)_nSH$ where n=1–8, phenylmethyl, 4-halophenylmethyl or $R_1+R_3=(CH_2)_3$; R₂ is alkyl, $(CH_2)_nOH$ where n=1–8, $(CH_2)_nSH$ where n=1–8, phenylmethyl, 4-halophenylmethyl or $R_2+R_4=(CH_2)_3$; R₁ and R₂ are a cyclic amine of the form $N(CH_2)_n$ where n=3–10; R₃ is H or $R_3+R_1=(CH_2)_3$; R₄ is H or $R_4+R_2=(CH_2)_3$; R₅ is H, alkyloxy or aryloxy; R₆ is H, $N(CH_3)_2$, alkyloxy or aryloxy; and R₇ is H, alkyloxy or aryloxy.

10. A nonlinear optical device comprising a composition of matter which exhibits a second-order nonlinear optical response, said composition having the formula:

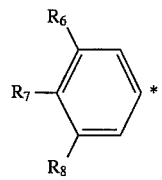

wherein A and B are selected from the group consisting of:

A is

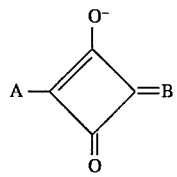

and B is

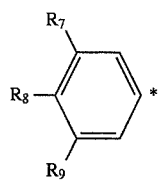

wherein * is the point of attachment, R₁ is alkyl,$(CH_2)_nOH$ where n=1–8, $(CH_2)_nSH$ where n=1–8, phenylmethyl, 4-halophenylmethyl or $R_1+R_3=(CH_2)_3$; R₂ is alkyl, $(CH_2)_nOH$ where n=1–8, $(CH_2)_nSH$ where n=1–8, phenylmethyl, 4-halophenylmethyl or $R_2+R_4=(CH_2)_3$; R₁ and R₂ is a cyclic amine of the form $N(CH_2)_n$ where n=3–10; R₃ is H or $R_3+R_1=(CH_2)_3$; R₄ is H or $R_4+R_2=(CH_2)_3$; R₅ is H, F, OH, SH, $CH_3$, $C_2H_5$, $OCH_3$, or $SCH_3$; R₆ is H, F, OH, SH, $CH_3$, $C_2H_5$, $OCH_3$, or $SCH_3$; R₇ is H, alkyloxy or aryloxy; R₈ is H, alkyloxy or aryloxy; and R₉ is H, alkyloxy or aryloxy;

A is

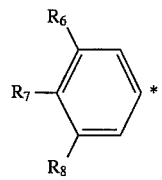

and B is

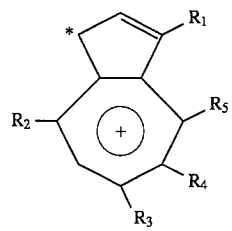

wherein * is the point of attachment, R₁ is H or methyl; R₂ is H or methyl; R₃ is H or methyl; R₄ is H or isopropyl; R₅ is H or methyl; R₆ is H, alkyloxy or aryloxy; R₇ is H, $N(CH_3)_2$, alkyloxy or aryloxy; and R₈ is H, alkyloxy or aryloxy;

A is

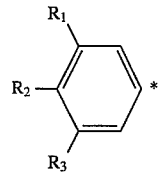

and B is

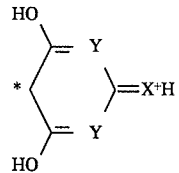

wherein * is the point of attachment, X is O or S; Y is CH or N; R₁ is H, alkyloxy or aryloxy; R₂ is H, $N(CH_3)_2$, alkyloxy or aryloxy; and R₃ is H, alkyloxy or aryloxy;

A is

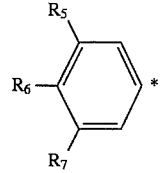

and B is

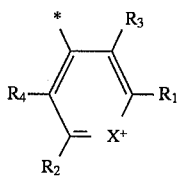

wherein * is the point of attachment, X is NR where R=alkyl, $(CH_2)_nOH$ where n=1–8, or $(CH_2)_nSH$ where n=1–8, or where X is O, S, Se, or Te; $R_1$ and $R_2$ are H, tert-butyl, phenyl 4-toluyl; $R_3$ and $R_4$ are H or $R_1$ and $R_3$ is HC=CH—HC=CH and $R_2$ is phenyl, or $R_1$, $R_3$, $R_2$ and $R_4$ are HC=CH—HC=CH; $R_5$ is H, alkyloxy or aryloxy; $R_6$ is H, $N(CH_3)_2$, alkyloxy or aryloxy; and $R_7$ is H, alkyloxy or aryloxy;

A is

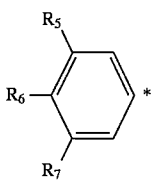

and B is

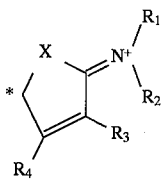

wherein * is the point of attachment, $R_1$ and $R_2$ are $(CH_2)_2O(CH_2)_2$, $(CH_2)_4$, or $(CH_2)_5$; $R_3$ is H, phenyl, or 3-methoxyphenyl; $R_4$ is H, phenyl, 4-bromophenyl, or 2-chlorophenyl; $R_5$ is H, alkyloxy or aryloxy; $R_6$ is H, $N(CH_3)_2$, alkyloxy or aryloxy; $R_7$ is H, alkyloxy or aryloxy; and X is O, S, Se, or Te;

A is

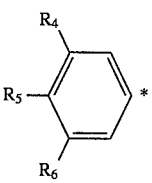

and B is

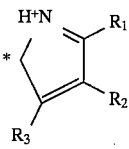

wherein * is the point of attachment, $R_1$ is methyl, $R_2$ is H, alkyl, acetyl, or alkoxycarbonyl; $R_3$ is H or methyl; $R_4$ is H, alkyloxy or aryloxy; $R_5$ is H, $N(CH_3)_2$, alkyloxy or aryloxy; and $R_6$ is H, alkyloxy or aryloxy;

A is

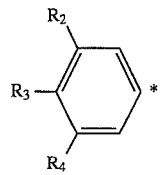

and B is

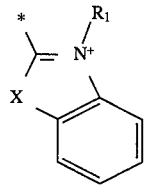

wherein * is the point of attachment, $R_1$ is alkyl; X is HC=CH, $(CH_3)_2C$, O, S, or Se; $R_2$ is H, alkyloxy or aryloxy; $R_3$ is H, $N(CH_3)_2$, alkyloxy or aryloxy; and $R_4$ is H, alkyloxy or aryloxy;

A is

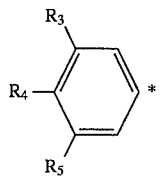

and B is

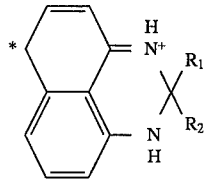

wherein * is the point of attachment, $R_1$ is H, alkyl, $(CH_2)_nOH$ where n=1–8, $(CH_2)_nSH$ where n=1–8, phenylalkyl, phenyl, phenylcarbonyl, aryl, arylcarbonyl, arylalkyl, alkoxycarbonylalkyl, phenylcarbonylalkyl, or arylcarbonylalkyl.; $R_2$ is H, alkyl, $(CH_2)_nOH$ where n=1–8, $(CH_2)_nSH$ where n=1–8, phenylalkyl, phenyl, phenylcarbonyl, aryl, arylcarbonyl, arylalkyl, alkoxycarbonylalkyl, phenylcarbonylalkyl, or arylcarbonylalkyl.; $R_3$ is H, alkyloxy or aryloxy; $R_4$ is H, $N(CH_3)_2$, alkyloxy or aryloxy; and $R_5$ is H, alkyloxy or aryloxy.

11. A nonlinear optical device according to claim 10 comprising a composition of matter which exhibits a second-order nonlinear optical response, said composition having the formula:

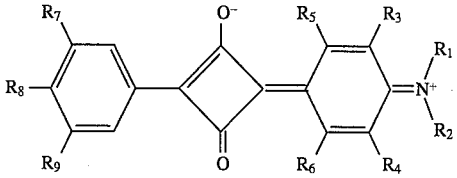

wherein $R_1$ is alkyl, $(CH_2)_nOH$ where n=1–8, $(CH_2)_nSH$ where n=1–8, phenylmethyl, 4-halophenylmethyl or $R_1+R_3=(CH_2)_3$; $R_2$ is alkyl, $(CH_2)_nOH$ where n=1–8, $(CH_2)_nSH$ where n=1–8, phenylmethyl, 4-halophenylmethyl or $R_2+R_4=(CH_2)_3$; $R_1$ and $R_2$ is a cyclic amine of the form $N(CH_2)_n$ where n=3–10; $R_3$ is H or $R_3+R_1=(CH_2)_3$; $R_4$ is H or $R_4+R_2=(CH_2)_3$; $R_5$ is H, F, OH, SH, $CH_3$, $C_2H_5$, $OCH_3$, or $SCH_3$; $R_6$ is H, F, OH, SH, $CH_3$, $C_2H_5$, $OCH_3$, or $SCH_3$; $R_7$ is H, alkyloxy or aryloxy; $R_8$ is H, alkyloxy or aryloxy; and $R_9$ is H, alkyloxy or aryloxy.

12. A nonlinear optical device according to claim 10 comprising a composition of matter which exhibits a second-order nonlinear optical response, said composition having the formula:

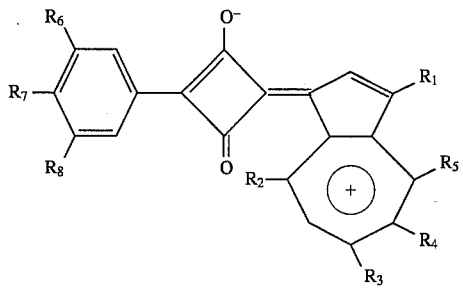

wherein $R_1$ is H or methyl; $R_2$ is H or methyl; $R_3$ is H or methyl; $R_4$ is H or isopropyl; $R_5$ is H or methyl; $R_6$ is H, alkyloxy or aryloxy; $R_7$ is H, $N(CH_3)_2$, alkyloxy or aryloxy; and R8 is H, alkyloxy or aryloxy.

13. A nonlinear optical device according to claim 10 comprising a composition of matter which exhibits a second-order nonlinear optical response, said composition having the formula:

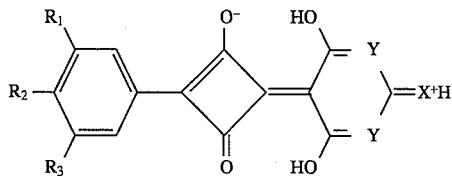

wherein X is O or S; Y is CH or N; $R_1$ is H, alkyloxy or aryloxy; $R_2$ is H, $N(CH_3)_2$, alkyloxy or aryloxy; and $R_3$ is H, alkyloxy or aryloxy.

14. A nonlinear optical device according to claim 10 comprising a composition of matter which exhibits a second-order nonlinear optical response, said composition having the formula:

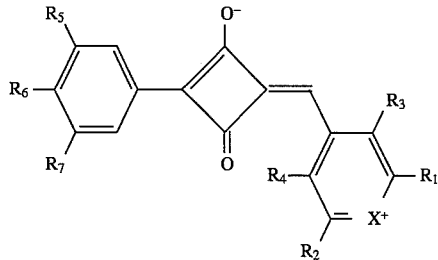

wherein X is NR where R=alkyl, $(CH_2)_nOH$ where n=1–8, or $(CH_2)_nSH$ where n=1–8, or where X is O, S, Se, or Te; $R_1$ and $R_2$ are H, tert-butyl, phenyl 4-toluyl; $R_3$ and R4 are H or $R_1$ and $R_3$ is HC=CH—HC=CH and $R_2$ is phenyl, or $R_1$, $R_3$, $R_2$ and R4 are HC=CH—HC=CH; $R_5$ is H, alkyloxy or aryloxy; $R_6$ is H, $N(CH_3)_2$, alkyloxy or aryloxy; and $R_7$ is H, alkyloxy or aryloxy.

15. A nonlinear optical device according to claim 10 comprising a composition of matter which exhibits a second-order nonlinear optical response, said composition having the formula:

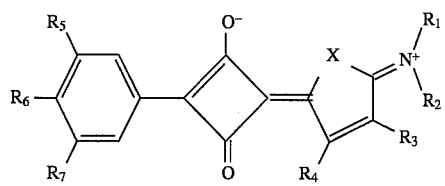

wherein $R_1$ and R2 are $(CH_2)_2O(CH_2)_2$, $(CH_2)_4$, or $(CH_2)_5$; $R_3$ is H, phenyl, or 3-methoxyphenyl; $R_4$ is H, phenyl, 4-bromophenyl, or 2-chlorophenyl; $R_5$ is H, alkyloxy or aryloxy; $R_6$ is H, $N(CH_3)_2$, alkyloxy or aryloxy; $R_7$ is H, alkyloxy or aryloxy; and X is O, S, Se, or Te;

16. A nonlinear optical device according to claim 10 comprising a composition of matter which exhibits a second-order nonlinear optical response, said composition having the formula:

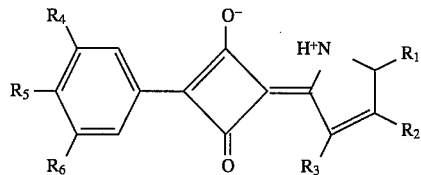

wherein $R_1$ is methyl, $R_2$ is H, alkyl, acetyl, or alkoxycarbonyl; $R_3$ is H or methyl; $R_4$ is H, alkyloxy or aryloxy; $R_5$ is H, $N(CH_3)_2$, alkyloxy or aryloxy; and $R_6$ is H, alkyloxy or aryloxy.

17. A nonlinear optical device according to claim 10 comprising a composition of matter which exhibits a second-order nonlinear optical response, said composition having the formula:

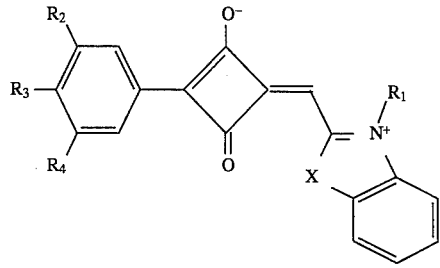

wherein $R_1$ is alkyl; X is HC=CH, $(CH_3)_2C$, O, S, or Se; $R_2$ is H, alkyloxy or aryloxy; $R_3$ is H, $N(CH_3)_2$, alkyloxy or aryloxy; and R4 is H, alkyloxy or aryloxy.

18. A nonlinear optical device according to claim 10 comprising a composition of matter which exhibits a second-order nonlinear optical response, said composition having the formula:

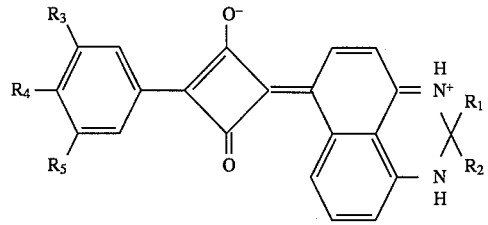

wherein $R_1$ is H, alkyl, $(CH_2)_nOH$ where n=1–8, $(CH_2)_nSH$ where n=1–8, phenylalkyl, phenyl, phenylcarbonyl, aryl, arylcarbonyl, arylalkyl, alkoxycarbonylalkyl, phenylcarbonylalkyl, or arylcarbonylalkyl.; $R_2$ is H, alkyl, $(CH_2)_nOH$ where n=1–8, $(CH_2)_nSH$ where n=1–8, phenylalkyl, phenyl, phenylcarbonyl, aryl, arylcarbonyl, arylalkyl, alkoxycarbonylalkyl, phenylcarbonylalkyl, or arylcarbonylalkyl.; R3 is H, alkyloxy or aryloxy; R4 is H, N(CH$_3$)$_2$, alkyloxy or aryloxy; and R$_5$ is H, alkyloxy or aryloxy.

19. A nonlinear optical device comprising a composition of matter which exhibits a second-order nonlinear optical response, said composition having the formula:

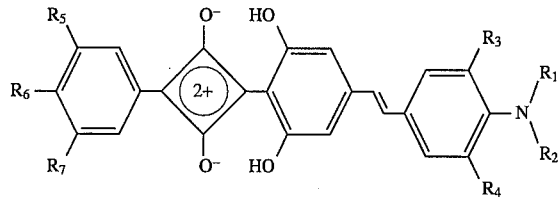

wherein R$_1$ is alkyl, (CH$_2$)$_n$OH where n=1–8, (CH$_2$)$_n$SH where n=1–8, phenylmethyl, 4-halophenylmethyl or R$_1$+R$_3$=(CH$_2$)$_3$; R$_2$ is alkyl, (CH$_2$)$_n$OH where n=1–8, (CH$_2$)$_n$SH where n=1–8, phenylmethyl, 4-halophenylmethyl or R$_2$ and R$_4$=(CH$_2$)$_3$; R$_1$+R$_2$ are a cyclic amine of the form N(CH$_2$)$_n$ where n=3–10; R$_3$ is H or R$_3$+R$_1$=(CH$_2$)$_3$; R$_4$ is H or R$_4$+R$_2$=(CH$_2$)$_3$; R$_5$ is H, alkyloxy or aryloxy; R$_6$ is H, N(CH$_3$)$_2$, alkyloxy or aryloxy; and R$_7$ is H, alkyloxy or aryloxy.

20. A composition of matter according to claim 9 where R$_1$=R$_2$=n-butyl, R$_3$=R$_4$=R$_5$=R$_7$=H, R$_6$=iso-pentyloxy.

21. A nonlinear optical device according to claim 2 wherein said device comprises a thin film or a crystal.

22. A nonlinear optical device according to claim 3 wherein said device comprises a thin film or a crystal.

23. A nonlinear optical device according to claim 4 wherein said device comprises a thin film or a crystal.

24. A nonlinear optical device according to claim 5 wherein said device comprises a thin film or a crystal.

25. A nonlinear optical device according to claim 6 wherein said device comprises a thin film or a crystal.

26. A nonlinear optical device according to claim 7 wherein said device comprises a thin film or a crystal.

27. A nonlinear optical device according to claim 8 wherein said device comprises a thin film or a crystal.

28. A nonlinear optical device according to claim 9 wherein said device comprises a thin film or a crystal.

* * * * *